(12) United States Patent
Sola I Caros et al.

(10) Patent No.: US 8,585,605 B2
(45) Date of Patent: Nov. 19, 2013

(54) METHOD AND APPARATUS FOR A CONTINUOUS NON-INVASIVE AND NON-OBSTRUSIVE MONITORING OF BLOOD PRESSURE

(75) Inventors: Josep Sola I Caros, Corcelles (CH); Hans-Andrea Loeliger, Zurich (CH)

(73) Assignee: CSEM Centre Suisse d'Electronique et de Microtechnique SA - Recherche et Developpement, Neuchatel (CH)

( * ) Notice: Subject to any disclaimer, the term of this patent is extended or adjusted under 35 U.S.C. 154(b) by 1043 days.

(21) Appl. No.: 12/341,619

(22) Filed: Dec. 22, 2008

(65) Prior Publication Data
US 2009/0163821 A1    Jun. 25, 2009

(30) Foreign Application Priority Data
Dec. 21, 2007  (EP) ................................ 07123934

(51) Int. Cl.
*A61B 5/02*       (2006.01)

(52) U.S. Cl.
USPC .......................................... 600/506; 600/485

(58) Field of Classification Search
None
See application file for complete search history.

(56) References Cited

U.S. PATENT DOCUMENTS

| | | | |
|---|---|---|---|
| 4,425,920 A | | 1/1984 | Bourland |
| 5,139,120 A | * | 8/1992 | Gomi ............................ 188/378 |
| 5,309,916 A | | 5/1994 | Hatschek |
| 5,590,649 A | * | 1/1997 | Caro et al. ..................... 600/300 |
| 6,371,921 B1 | * | 4/2002 | Caro et al. ..................... 600/485 |
| 6,485,431 B1 | | 11/2002 | Campbell |
| 6,648,828 B2 | * | 11/2003 | Friedman et al. ............. 600/506 |
| 2006/0217616 A1 | | 9/2006 | Kuchler |

FOREIGN PATENT DOCUMENTS

EP        1344489         9/2003

OTHER PUBLICATIONS

Search Report dated Jun. 4, 2008 in Priority application , 2 pages.
Bernd et al., "Nonlinear Black Box Modelling—Fuzzy Networks versus Neural Networks", Neural Comput & Applications, 1999, vol. 8, pp. 151-162.

* cited by examiner

*Primary Examiner* — Anne Gussow
*Assistant Examiner* — Channing S Mahatan
(74) *Attorney, Agent, or Firm* — Young & Thompson (57) ABSTRACT

The invention provides a method and an apparatus for a continuous non-invasive and non-obstrusive monitoring of blood pressure. The method comprises the steps of: a) measuring the value (PW) of a Pulse Wave parameter, equal to or derived from the Pulse Wave Velocity (PWV) parameter of a segment of the arterial tree of a subject, b) measuring the value (CO) of the Cardiac Output parameter, and c) determining the value (BP) of the blood pressure that satisfies $$BP = \underset{BP}{\mathrm{argmin}}\, d(PW, \widehat{PW}(CO, BP)),$$

where PW is the value measured in step a), $\widehat{PW}(CO, BP)$ corresponds to a predicted value of the Pulse Wave parameter computed according to a model of the segment of the arterial tree, the value (CO) of the Cardiac Output parameter measured in step b) and an hypothesized value of the blood pressure.

17 Claims, 2 Drawing Sheets

METHOD AND APPARATUS FOR A CONTINUOUS NON-INVASIVE AND NON-OBSTRUSIVE MONITORING OF BLOOD PRESSURE

TECHNICAL FIELD

This invention relates to a method and an apparatus for a continuous non-invasive and non-obstrusive monitoring of blood pressure (BP).

BACKGROUND OF THE INVENTION

Beat-to-Beat blood pressure (BP) measurements are commonly achieved in clinical practice by introducing an intra-arterial catheter. This method provides accurate and instantaneous blood pressure (BP) measurements. A disadvantage of this method is that it is invasive and can be used only in clinical practice.

For this reason, methods have been developed in order to achieve an accurate fully continuous and comfortable measurement of arterial blood pressure (BP) in the field of clinical and ambulatory monitoring. However, none of the current state-of-the-art measurements techniques achieve such requirements.

There are currently only two methods that are recognized as standard methods in non-invasive assessment of the blood pressure (BP): the oscillometric technique already introduced in 1876 by Marey and the auscultatory method introduced in 1905 by Korotkoff. It is even more remarkable the fact that Koroktoff's method has little evolved since its invention and it still requires the presence of a well trained observer equipped with a stethoscope. Therefore, with such method, important deviations are observed being related to observer's judgment.

Recently, the oscillometric technique has lead to a generation of low-cost automated blood pressure (BP) monitors boosting the field of ambulatory blood pressure (BP) monitoring. Although such devices allow the self-measurement of blood pressure (BP) from the upper-arm or the wrist even in noisy conditions and during motion, accuracy might be compromised due to wrong body or arm position. Moreover, two main factors limit the real ambulatory use of oscillometric devices: the too long measurement time required (approx. 30 seconds) and the decreased measurement frequency due to comfort issues (15 to 30 minutes).

However, automated oscillometric devices remain the only choice in ambulatory blood pressure (BP) measurement and they are currently used in most of the ambulatory and epidemiological studies. But, because of the very low sampling frequencies of the oscillometeric method (typically, one measurement every 30 minutes), problems related to oversmoothing, aliasing and overmodeling might appear.

Other new methods for the non-invasive assessment of arterial blood pressure (BP) have been developed.

The arterial tonometry is a method based on compressing and partially flattening a superficial artery against its underlying bone. A pressure sensor translates then the intra-arterial forces to arterial pressure waveforms. However, the translation requires a calibration procedure to provide absolute blood pressure (BP) measurements. Some commercial devices are already available in clinical practice and require intermittent calibrations via arm-cuff oscillometric technique. However, aside from the problems related to the sensibility of the approach to motion artefacts, the accuracy of such devices has been continuously contested.

An evolved solution to applanation tonometry has also been introduced by MEDWAVE. By gently compressing and decompressing the radial artery during a period of 12 to 15 beats, a transducer identifies the zero-load state on the artery wall and estimates systolic blood pressure (BP) out of it. However, the device is not able to cope with motion artifacts during the measurement and requires subjects to remain still.

In the Volume-Clamp method, a small cuff incorporating a photo-plethysmograph device is placed on a finger. The diameter of the arteries under the cuff is kept constant (clamped), despite of the changes in arterial pressure during each heart beat, i.e. the pressure exerted by the cuff is pneumatically controlled to track the photoplethysmographic signal in real-time and assure a constant light transmission through the phalanx. The servo-controlled cuff pressure follows then the instantaneous arterial pressure waveform. The accuracy and reproducibility of the method has been demonstrated in several clinical studies. However, evidences exist on problems associated to the automatic recalibration and the overestimation of systolic pressure.

Moreover, the volume-clamp method remains an occlusive method that can lead to periods of venous congestion during prolonged use. Additionally some models have been proposed to reconstruct brachial and central pressure from finger measurements.

Another method is based on the Pulse Wave Velocity (PWV). It is known that the velocity of pressure pulses travelling through an artery is correlated with its elasticity (or stiffness). Already in 1878 Moens and Korteweg independently came out with a close expression relating the velocity of pulse waves (c) in a thin, infinite elastic tube with its mechanical properties. According to their model, c is determined by the relationship $$c^2 = \frac{tE}{\rho d}$$

where c is the so-called Pulse Wave Velocity, t, E, and d are respectively the thickness, the Young's modulus and the diameter of the tube, and p is the density of the fluid in the tube.

Later on, in 1961, Bergel experimentally determined and quantified that the Young's modulus of an artery in animals is strongly dependent on the internal pressure in the vessel. Hence, one can rewrite the above equation as:

$$c^2 = \frac{t}{\rho d} f(BP)$$

where BP is the blood pressure, and f (BP) depicts the dependency of E on BP, and it can be experimentally determined. Several authors have considered f (BP) to be an exponential function of BP. This equation shows that by fixing the value of $$\frac{t}{\rho d},$$

there exist a one-to-one correspondence between c and BP: that is, once the values of $$\frac{t}{\rho d}$$

and the function f (BP) have been fixed it is possible to obtain blood pressure (BP) from pulse wave velocity (c) measurements. Such method is described for example in U.S. Pat. No. 6,599,251. According to this method:
an initial guess on the values of $$\frac{t}{\rho d}$$

and f (BP) is done during a calibration procedure,
a sensing methodology continuously computes the velocity of the pulse wave (c) generated at each heart beat through a segment of the arterial tree,
assuming the calibration values to be constant, the measured values of c are used to continuously estimate BP.

However, the method describes in U.S. Pat. No. 6,599,251 does not take in account the dynamic adaptation of $$\frac{t}{\rho d}.$$

Indeed, the three parameters do get continuously modified in a living cardio vascular system. Some recent studies have measured the modifications of diameter in human arteries during different cardio vascular adaptations in-vivo. The change in diameter of radial artery is assessed using an echo-Doppler device: during the recordings, the diameter of the radial artery was found to increase from 2 mm to 2.2 mm (10% increase). With another method measuring the changes in diameter of the carotid artery by an ultrasound imaging technique, it has been found that the diameter is increased from 6 to 7mm (16% increase) when the blood pressure (BP) is increased by 30 mm Hg.

EP 1 344 489 discloses a continuous non-invasive process for measuring blood pressure using impedance plethysmography. This process comprises a step for calculating the blood volume change from the first pulse and a step for calculating the blood volume change from the second pulse. However, if blood pressure derivates due to changes in vessels compliance, a recalibration is needed to compensate for these changes employing a simultaneous measurement of stroke volume and blood pressure measurement. For each recalibration, an oscillometeric blood pressure measurement or a manual auscultatory method is used.

U.S. Pat. No. 5,309,916 discloses a device for measuring the blood pressure using local measurements of pulse wave velocity and blood flow velocity. Accordingly, the local blood pressure of the vessels underneath the sensor means is calculated as a pre-calibrated function of the joint variation of pulse wave velocity and blood flow velocity at the measurement site. Therefore, such a device requires the continuous measurement of blood flow velocity, or equivalently, the continuous measurement of rate of blood flow and the diameters of the vessels involved in the measurements.

DE 102 49 863 discloses a non-invasive blood pressure measurement method in which the difference between a signal measured using an impedance cardiograph and that determined using an optical or acoustic peripheral pulse wave is determined. Such method does not take into account the elasticity of the vessels. Therefore, such a method requires frequent recalibration.

SUMMARY OF THE INVENTION

The present invention provides blood pressure (BP) measurement method and apparatus which allow to avoid the disadvantages of the prior art.

In one aspect, the invention provides a method for a continuous non-invasive and non-obstrusive monitoring of blood pressure (BP) which allows to obtain accurate measurements similar to those obtained with an invasive method.

Accordingly, a method for a continuous non-invasive and non-obstrusive monitoring of blood pressure (BP) according to one aspect of the invention, comprises the steps of:
a) measuring the value (PW) of a Pulse Wave parameter, equal to or derived from the Pulse Wave Velocity (PWV) parameter of a segment of the arterial tree of a subject,
b) measuring the value (CO) of the Cardiac Output parameter,
c) determining the value (BP) of the blood pressure that satisfies $$BP = \operatorname*{argmin}_{BP} d(PW, \widehat{PW}(CO, BP)),$$

where PW is the value measured in step a), $\widehat{PW}$ (CO, BP) corresponds to a predicted value of the Pulse Wave parameter computed according to a model of the segment of the arterial tree, the value (CO) of the Cardiac Output parameter measured in step b) and an hypothesized value of the blood pressure.

That means that said step c) is a step of determining the value (BP) of blood pressure that minimizes the distance between the value (PW) of the Pulse Wave parameter measured in step a) and a predicted value of the Pulse Wave parameter computed according to a model of the segment of the arterial tree, the value (CO) of the Cardiac Output measured in step b) and an hypothesized value of the blood pressure.

In some embodiments, the distance between PW and $\widehat{PW}$ is a p-norm Euclidian distance, where p is an integer greater than or equal to 1.

Preferably, the different steps are repeated in such a way to obtain a series of consecutively determined values BP of the blood pressure which is constrained in frequency and/or dynamic range.

Preferably, the hypothesized value of the blood pressure used in step c) is determined from an hypothesized value of at least one of geometric and elastic characteristics of the involved vessels in the segment of the arterial tree, and said step c) comprises the steps of:
i) hypothesizing a value of at least one of geometric and elastic characteristics of the involved vessels in the segment of the arterial tree,
ii) from said hypothesized value of said geometric and elastic characteristic, determining an expected value of the Pulse Wave parameter by using a model relating the Pulse Wave parameter, the Cardiac Output parameter and said geometric and elastic characteristic, iii) computing the distance between said expected Pulse Wave parameter value and said measured Pulse Wave parameter value (PW), iv) repeating steps i), ii), and iii) until the distance between the expected Pulse Wave parameter value and the measured Pulse Wave parameter value (PW) is minimized in order to determine an estimated value of said geometric and elastic characteristic, v) from said estimated value of the geometric and elastic characteristic determined in step iv), determining the value (BP) of the blood pressure by using a model relating the blood pressure, said Cardiac Output parameter, and said geometric and elastic characteristic.

In some embodiments, the Pulse Wave parameter may be the Pulse Wave Velocity (PWV) parameter or the Pulse Transit Time (PTT) parameter.

Preferably, said geometric and elastic characteristic is the diameter of the vessels in the segment of the arterial tree.

In some embodiments, the model of the segment of the arterial tree, the model relating the Pulse Wave parameter, the Cardiac Output parameter and said geometric and elastic characteristic, or the model relating the blood pressure, the Cardiac Output parameter and said geometric and elastic characteristic, is theoretical.

In other embodiments, the model of the segment of the arterial tree, the model relating the Pulse Wave parameter, the Cardiac Output parameter and said geometric and elastic characteristic, or the model relating the blood pressure, the Cardiac Output parameter and said geometric and elastic characteristic, is empirical. Preferably, the Pulse Wave parameter measured in step a) is measured only by means of optic and electric sensing technologies.

Preferably, the Cardiac Output parameter measured in step b) is measured only by means of electric sensing technologies, by measuring the Heat Rate (HR) parameter and the Stroke Volume (SV) parameter.

Depending on the models used in the invention, the used parameters are also measured only by means of optic and electric sensing technologies.

In particular, the optic technology is Photoplethysmography (PPG) and the electric technologies are Electrocardiography (ECG) and Impedance Pleythysmography (IPG).

In a preferred embodiment, the method of the invention further comprises a step d) of storing and/or displaying the value (BP) of blood pressure determined in step c).

In another preferred embodiment, the method of the invention further comprises a step e) of determining the Total Peripheral Resistance (TPR) parameter from the value (BP) of the blood pressure determined in step c).

In another preferred embodiment, the method of the invention further comprises a step f) of simultaneously storing and/or displaying several cardiovascular parameters selected from the group comprising the determined Total Peripheral Resistance (TPR), the determined value (BP) of the blood pressure, the value (CO) of the Cardiac Outpout parameter.

In another aspect, the invention provides an apparatus for a continuous non-invasive and non-obstrusive monitoring of blood pressure, especially by carrying out the method described above, wherein said apparatus comprises:

means for measuring the Pulse Wave parameter, equal to or derived from the Pulse Wave Velocity (PWV) parameter of a segment of the arterial tree of a subject, and for providing at least one signal representative of said Pulse Wave parameter, means for measuring the Cardiac Output parameter, and for providing at least one signal representative of said Cardiac Output parameter, and means for determining the value of blood pressure (BP) that satisfies, $$BP = \operatorname*{argmin}_{BP} d(PW, \widehat{PW}(CO, BP))$$

where PW is the measured value of the Pulse Wave parameter, $\widehat{PW}$ (COBP) corresponds to a predicted value of the Pulse Wave parameter computed according to a model of the segment of the arterial tree, the measured value (CO) of the Cardiac Output parameter and an hypothesized value of the blood pressure.

Preferably, the hypothesized value of the blood pressure is determined from a hypothesized value of at least one of geometric and elastic characteristics of the involved vessels in the segment of the arterial tree, and the apparatus further comprises:

processing means for hypothesizing a value of at least one of geometric and elastic characteristics of the involved vessels in the segment and, from said hypothesized value of said geometric and elastic characteristic, determining an expected value of the Pulse Wave parameter by using a model relating the Pulse Wave parameter, the Cardiac Output parameter and said geometric and elastic characteristic, processing means for comparing said expected Pulse Wave parameter value to said signal representative of the measured Pulse Wave parameter value and computing the distance between said expected Pulse Wave parameter value and said measured Pulse Wave parameter value (PW), processing means for repeating the determination of an expected value of the Pulse Wave parameter from a hypothesized value of said geometric and elastic characteristic and the comparison of said expected Pulse Wave parameter value to said signal representative of the measured Pulse Wave parameter value, until the distance between the expected Pulse Wave parameter value and the measured Pulse Wave parameter value is minimized in order to determine an estimated value of said geometric and elastic characteristic, computing means for determining the value (BP) of the blood pressure from said estimated value of said geometric and elastic characteristic by using a model relating the blood pressure, said Cardiac Output parameter, and said geometric and elastic characteristic, means for storing and/or displaying the determined value (BP) of the blood pressure.

In some embodiments, the Pulse Wave parameter may be the Pulse Wave Velocity (PWV) parameter or the Pulse Transit Time (PTT) parameter.

Preferably, the geometric and elastic characteristic is the diameter of the vessels in the segment.

In some embodiments, the model of the segment of the arterial tree, the model relating the Pulse Wave parameter, the Cardiac Output parameter, and said geometric and elastic characteristic, or the model relating the blood pressure, the Cardiac Output parameter and said geometric and elastic characteristic, is theoretical.

In other embodiments, the model of the segment of the arterial tree, the model relating the Pulse Wave parameter, the Cardiac Output parameter and said geometric and elastic characteristic, or the model relating the blood pressure, the Cardiac Output parameter and said geometric and elastic characteristic is empirical. Preferably, means for measuring the Pulse Wave Velocity (PWV) parameter use only optic and electric sensing technologies and means for measuring the Cardiac Output parameter use only electric sensing technologies.

In particular, the optic technology is Photoplethysmography (PPG) and the electric technologies are Electrocardiography (ECG) and Impedance Pleythysmography (IPG).

In a preferred embodiment, the apparatus of the invention further comprises means for computing the Total Peripheral Resistance (TPR) parameter from the determined value (BP) of the blood pressure.

In another preferred embodiment, the means for storing and/or displaying the determined value (BP) of the blood pressure comprise means for simultaneously storing and/or displaying several cardiovascular parameters selected from the group comprising the determined Total Peripheral Resistance (TPR), the determined value (BP) of the blood pressure, the value (CO) of the Cardiac Output parameter.

The method and the apparatus according to the invention allow to take in account the modifications of diameter in arteries of a living cardio vascular system and to improve the accuracy of the determination of the blood pressure (BP).

The method and the apparatus according to the invention allow also to continuously track the state of the cardiovascular system by estimating different parameters, and to independently identify the cardiac and angiographic adaptations of the cardiovascular system.

DETAILED DESCRIPTION

The method of the invention is based on the relationship between the Pulse Wave Velocity (PWV), the Cardiac Output (CO) and the blood pressure (BP), and on the fact that at least one of the geometric and elastic characteristics of the vessels in the segment is one of the parameters which can modify this relationship.

In the present description, the Pulse Wave Velocity (PWV) is used as the Pulse Wave parameter. It is obvious that the description of the invention is the same with the Pulse Transit Time (PTT), where PTT=L/PWV, L being the path length of the segment of the arterial tree.

Such a geometric and elastic characteristic is for example the diameter of the vessels in the segment. Therefore, the invention will be described below by using the diameter of the vessels in the segment as such geometric and elastic characteristic. But it is obvious that another geometric and elastic characteristic of the vessels in the segment can be used, such as the thickness of the vessels involved in the segment of the arterial, the modulus of elasticity of the vessels involved in the segment of the arterial, the dependency of modulus of elasticity of the vessels involved in the segment of the arterial and the intravascular pressure at such vessels, and the density of blood in the vessels involved in the segment of the arterial.

According to the invention, the first step a) of the method is a step of measuring the Pulse Wave Velocity (PWV) parameter of a segment of the arterial tree of a subject. Preferably, the continuous measuring of Pulse Wave Velocity (PWV) in ambulatory environments uses optic and electric sensing technologies, such as Photoplethysmography (PPG), Electrocardiography (ECG) and Impedance Pleythysmography (IPG).

Photoplethysmography (PPG) refers to a sensing technique that exploits the change of light absorption that is observed in human's tissue due to changes in blood volume. More specifically, each time a heart beat occurs, a pressure wave travels along the arterial tree increasing the diameter of each arterial segment when passing through it. If one analyses the absorption of light in a given arterial site, one might detect the arrival of the pressure wave at each heart beat. The absorption of light is easily determined by injecting a light beam through the skin and by detecting the reflected or transmitted part of it by a photo-diode placed over the skin. LED or LASER emitters on the near-infrared range are commonly used due to the absorption characteristics of water and hemoglobin at those wavelengths.

The velocity of a pulse wave (PWV) through a segment of the arterial tree might be determined by placing at least two Photoplethysmography sensors at different sites of the segment. By knowing the distance between both sites, the detection of the arrival of the pressure wave on each site leads to the knowledge of the propagation velocity.

In order to reduce the high sensibility of Photoplethysmography technology to motion artifacts (displacements of the optical probe, venous blood displacement and muscle contraction), it is preferable to combine Photoplethysmography technology with Electrocardiography for synchronization purposes.

The velocity of the pulse wave (PWV) is therefore determined by comparing the onset of the electrical activation of the heart (proximal point) to the onset of the pulse pressure in a given point of the arterial tree (distal point). Using this configuration, the obtained transit time includes the contribution of all the arterial segments between the aorta and the distal measurement point.

In order to improve the accuracy of the measurement, it is preferable to combine Photoplethysmography (PPG) technology and Electrocardiography (ECG) with Impedance Pleythysmography (IPG), which is a method of determining changing tissue volumes in the body, based on the measurement of electric impedance at the body surface. This allows to take in account, in the PWV calculation, the delay between the onset of the electrical activation of the heart and start of the ventricular ejection. This delay is commonly depicted as Pre-Ejection Period (PEP). This delay can by computed by Impedance Plethysmography (IPG).

It is obvious that other methods, allowing to obtain continuous accurate measurements of Pulse Wave Velocity (PWV), can be used.

According to the invention, the following step b) of the method is a step of measuring the value (CO) of the Cardiac Output parameter.

The Cardiac Output parameter is commonly assessed in clinical practice and different noninvasive measurements can be used. According to a preferred measurement, the value (CO) of the Cardiac Output parameter is determined from the cardiovascular parameters Heat Rate (HR) and Stroke Volume (SV) and is defined by the equation CO=HRSV.

Preferably, the heart rate (HR) and the Stroke Volume (SV) parameters are measured only by means of electric sensing technologies. The heart rate (HR) can be measured for example by means of Electrocardiography (ECG) and the Stroke Volume (SV) can be measured by means of Impedance Pleythysmography (IPG), which are the same sensing technologies used to measure the Pulse Wave Velocity (PWV).

According to the invention, the following step c) of the method is a step of determining the value (BP) of the blood pressure that satisfies $$BP = \underset{BP}{\mathrm{argmin}}\, d(PW, \widehat{PW}(CO, BP))$$

where PW is the value measured in step a), $\widehat{PW}(CO, BP)$ corresponds to a predicted value of the Pulse Wave parameter computed according to a model of the segment of the arterial tree, the value (CO) of the Cardiac Output parameter measured in step b) and an hypothesized value of the blood pressure.

For this step c), the hypothesized value of the blood pressure may be determined from an hypothesized value of the diameter of the vessel, and a model relating the Pulse Wave Velocity (PWV), the Cardiac Output parameter and the diameter of the vessel may be used to determine an expected value of the Pulse Wave Velocity (PWV) from said hypothesized value of the diameter of the vessels in the segment, as requested by the steps i) and ii).

Said model can be an empirical model obtained from in-vivo data previously measured on one or several subjects.

Said model can be also a theoretical model relating the Pulse Wave Velocity (PWV), the Cardiac Output parameter, and the diameter of the vessels in the segment.

Preferably, said theoretical model is based on the relationship between Pulse Wave Velocity (PWV) and the blood pressure according to Moens and Korteweg and to Bergel. This relationship gives an equation relating the Pulse Wave Velocity (PWV), the blood pressure (BP) and the diameter d of the vessels which is:

$$PWV^2 = \frac{tE_0 e^{BP}}{\rho d}$$

where t is the thickness of the vessel wall; $E_0$ is the zero-pressure modulus of the vessel wall, $\rho$ is the density of blood, d is the diameter of the vessels in the segment, and BP is the blood pressure.

One skilled in the art knows that BP=COTPR, where CO is the Cardiac Output, and TPR is the Total Peripheral Resistance.

The Cardiac Output parameter has been described above.

The Total Peripheral Resistance (TPR) is extensively used in medical physiology because of its ability of describing the overall effect that the arterial tree has in the control of blood pressure. It should be defined as a function of the diameter d of the vessels in the segment. According to the Poiseuille's model, $$TPR \simeq \mu \frac{k}{d^4},$$

where k depends on the geometry of the vessel and $\mu$ is the viscosity of the blood.

It is obvious that other models defining the Total Peripheral Resistance (TPR) as a function of the diameter of the vessel can be used.

According to the models previously described, the equation relating the Pulse Wave Velocity and the diameter of the vessel is:

$$PWV^2 = \frac{tE_0 e^{HRSV\mu \frac{k}{d^4}}}{\rho d}$$

It is obvious that another equation could be obtained by using other theoretical models.

According to the following step iii) of the method for determining the value (BP) of the blood pressure, the Pulse Wave Velocity (PWV) value, estimated with the model described above and the hypothesized diameter, is compared to the Pulse Wave Velocity (PWV) value measured in step a) by Photoplethysmography (PPG), Electrocardiography (ECG) and Impedance Pleythysmography (IPG).

According to the following step iv) of the method for determining the value (BP) of the blood pressure, steps i), ii) and iii) are repeated until the distance between the expected Pulse Wave Velocity (PWV) value and the measured Pulse Wave Velocity (PWV) value is minimized in order to determine an estimated value of the diameter.

A preferred minimization method is the so-called steepest descent algorithm described for example in *Statistical and Adaptive Signal Processing*, D. M. Manolaskis McGraw-Hill, 2000, p. 516-524.

Different mathematical methods can be used to determine Pulse Wave Velocity (PWV) from the hypothesis of the diameter and the comparison to the measured value of Pulse Wave Velocity (PWV).

A preferred mathematical model is for example a black box model and a method based on Neural Networks. Such method is for example described in *Nonlinear Black Box Modelling— Fuzzy Networks versus Neural Networks*, T. Bernd, M. Kleutges and A. Kroll, Neural Computing & Applications, 8, p. 51-162.

According to the following step v) of the method for determining the value (BP) of the blood pressure, the value (BP) of the blood pressure is determined from the estimated value of the diameter determined in step iv), by using a model relating to the blood pressure and the diameter of the vessel.

Said model can be an empirical model obtained from in-vivo data previously measured on one or several subjects.

Said model can be also a theoretical model giving an equation relating the blood pressure (BP) and the diameter of the vessel. If the same theoretical model as described above is used, said equation relating the blood pressure (BP) and the diameter d of the vessel is:

$$BP = HRSV\mu \frac{k}{d^4}$$

where HR, SV, $\mu$ and k have been defined above.

As explained above, the parameters HR and SV for determining the blood pressure (BP) are measured only by means of electric sensing technologies.

The different steps of the method of the invention are carried out continuously in order to obtain a continuous monitoring of the blood pressure (BP). The series of consecutively determined values BP of the blood pressure is constrained in frequency and/or dynamic range.

According to the following step d) of the method of the invention, the value (BP) of the blood pressure determined in step c) is stored and displayed, for example on a screen, as a graph showing the values (BP) of the blood pressure as a function of time.

According to another step e) of the method of the invention, the Total Peripheral Resistance (TPR) parameter is determined from the value (BP) of the blood pressure determined in step c) or from the estimated value of the diameter determined in step iv).

If the same theoretical model as described above is used, the Total Peripheral Resistance (TPR) parameter is for example determined from the value (BP) of the blood pressure determined in step c) by performing the calculation:

$$TPR = \frac{BP}{HRSV}$$

where HR and SV have been defined above.

Therefore, a continuous monitoring of the Total Peripheral Resistance (TPR) is obtained.

According to the step f) of the method of the invention, the determined Total Peripheral Resistance (TPR), the determined value (BP) of the blood pressure, and value (CO) of the Cardiac Output parameter are simultaneously stored and/or displayed, for example on the same screen, as three graphs showing these values a function of time.

Therefore the method allows to continuously observe the state of the cardiovascular system.

The apparatus according to the present invention and for which the diameter of the vessels in the segment has been chosen as the geometric and elastic characteristic, comprises:
  means for measuring the Pulse Wave Velocity (PWV) parameter, and for providing at least one signal representative of said Pulse Wave Velocity (PWV),
  means for measuring the Cardiac Output parameter, and for providing at least one signal representative of said Cardiac Output parameter,
  processing means for hypothesizing a value of the diameter of the vessels in the segment and, from said hypothesized value of the diameter, determining an expected value of the Pulse Wave Velocity (PWV) by using a model relating the Pulse Wave Velocity (PWV), the Cardiac Output parameter and the diameter of the vessels,
  processing means for comparing said expected Pulse Wave Velocity (PWV) value to said signal representative of the measured Pulse Wave Velocity (PWV) value and computing the distance between said expected Pulse Wave parameter value and said measured Pulse Wave parameter value (PW),
  processing means for repeating the determination of an expected value of the Pulse Wave Velocity (PWV) from a hypothesized value of the diameter and the comparison of said expected Pulse Wave Velocity (PWV) value to said signal representative of the measured Pulse Wave Velocity (PWV) value, until the distance between the expected Pulse Wave Velocity (PWV) value and the measured Pulse Wave Velocity (PWV) value is minimized in order to determine an estimated value of the diameter,
  computing means for determining the value (BP) of the blood pressure from said estimated value of the diameter by using a model relating the blood pressure, the Cardiac Output parameter and the diameter of the vessels in the segment,
  means for computing the Total Peripheral Resistance (TPR) parameter from the determined value (BP) of the blood pressure or from the estimated value of the diameter,
  means for storing and displaying the determined value (BP) of the blood pressure, and more particularly means for simultaneously displaying the determined Total Peripheral Resistance (TPR), the determined value (BP) of the blood pressure , and the measured value (CO) of the Cardiac Output parameter as a function of time.

For measuring the Cardiac Output parameter, and for providing at least one signal representative of said Cardiac Output parameter, the apparatus of the invention comprises means for measuring the cardiovascular parameters Heat Rate (HR) and Stroke Volume (SV) and for providing the signals representative of said Heat Rate (HR) and Stroke Volume (SV) parameters to the processing means in order to determine the expected value of the Pulse Wave Velocity and then the value (BP) of the blood pressure, the value of the Total Peripheral Resistance (TPR) and the value (CO) of the Cardiac Output parameter.

As explained above, the means for measuring the Pulse Wave Velocity (PWV) parameter, the Heat Rate (HR) parameter and the Stroke Volume (SV) parameter are based preferably only on the optic Photoplethysmography (PPG) technology and on the electric Electrocardiography (ECG) and Impedance Pleythysmography (IPG) technologies.

The different sensors used by these technologies can be placed on the thorax of the subject. They can be for example integrated in the fabrics of a garment.

The invention proposes a method and an apparatus allowing a continuous non-invasive and non-obstrusive monitoring of a set of cardiovascular parameters by using only optic and electric sensing technologies, and without true measuring of the blood pressure, which could be invasive for the subject.

The present invention was evaluated by using a theoretical model such as described above, and illustrated by FIG. 3.

Figure 3:
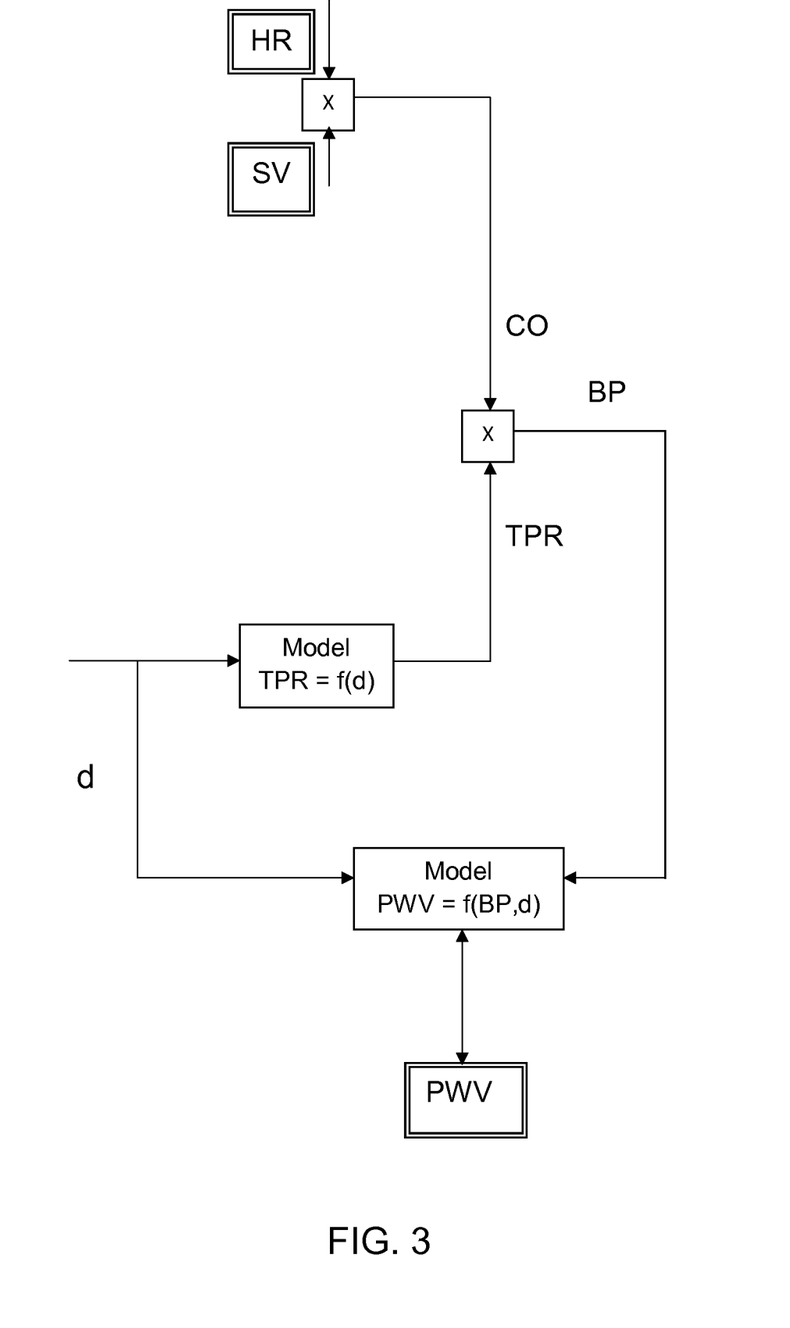
FIG. 3 is a flow chart illustrating a preferred embodiment of the method of the invention.

During 25 minutes, the temporal evolution of the blood pressure (BP), the Cardiac Output (CO) and the Total Peripheral Resistance (TPR) of a subject were determined with the method of the invention. At minute 10, the subject was asked to perform a handgrip at 40% of the Maximum Voluntary Contraction (MVC) during two minutes. According to the model, the tested method comprised the steps of:
  a) continuously measuring the Pulse Wave Velocity (PWV), the Heart Rate (HR) and the Stroke Volume (SV) by means of Photoplethysmography (PPG), Electrocardiography (ECG) and Impedance Pleythysmography (IPG), the sensors being placed on the thorax of the subject,
  b) hypothesizing a value (d) of the diameter of the vessel,
  c) from said hypothesized value (d) of the diameter, determining an expected value of the Pulse Wave Velocity (PWV) by performing the calculation:

$$PWV^2 = \frac{tE_0 e^{HRSV\mu\frac{k}{d^4}}}{\rho d}$$

where t, $E_0$, $\rho$, $\mu$, k have been defined above, and have been tuned according to subject's characteristics,
  d) comparing said expected Pulse Wave Velocity (PWV) value to said measured Pulse Wave Velocity (PWV) value, e) repeating steps b, c and d until the distance between the expected Pulse Wave Velocity (PWV) value and the measured Pulse Wave Velocity (PWV) value is minimized in order to determine an estimated value of the diameter, f) from said estimated value of the diameter determined in step e), determining the value (BP) of the blood pressure by performing the calculation:

$$BP = HRSV\mu \frac{k}{d^4}$$

where μ and k have been defined above, HR and SV have been previously measured, h) determining the Total Peripheral Resistance (TPR) from the value (BP) of the blood pressure determined in step f) by performing the calculation:

$$TPR = \frac{BP}{HRSV}$$

where HR and SV have been previously measured, i) simultaneously displaying on the same screen the determined Total Peripheral Resistance (TPR), the blood pressure (BP), and the Cardiac Output (CO) (obtained from HR and SV), as a function of time.

A BIOPAC platform was used to record ECG, IPG and PPG signals.

Figure 1:
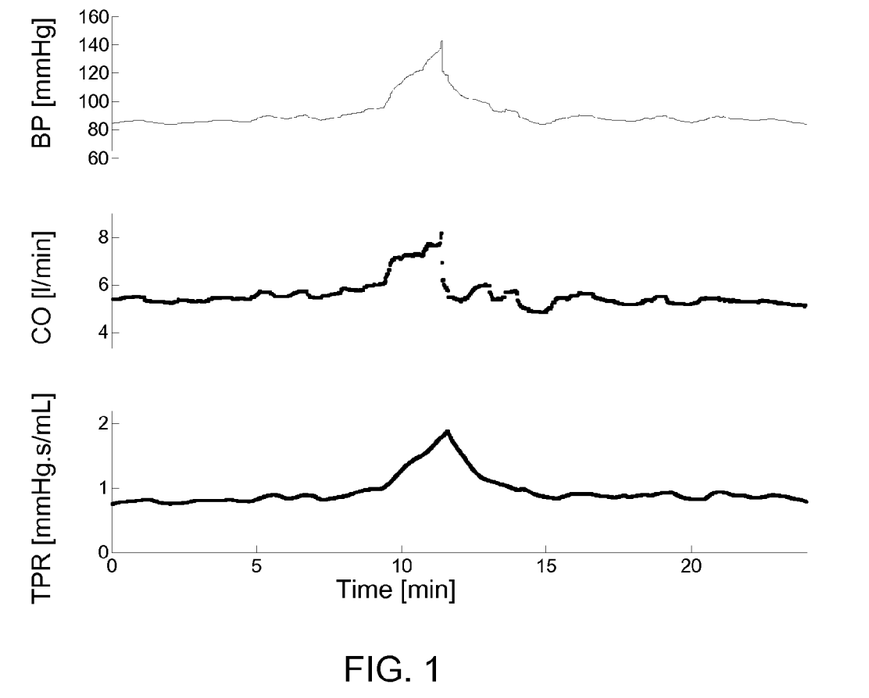
FIG. 1 is a diagram illustrating the values of blood pressure, Cardiac Output and Total Peripheral Resistance parameters obtained with the method according to the present invention.

FIG. 1 illustrates the results obtained by the method of the invention and shows the three graphs given the blood pressure (BP), the Total Peripheral Resistance (TPR) and the Cardiac Output (CO) as a function of time.

The method provides a picture of the continuous adaptation of the cardiovascular system and allows to independently identify its cardiac and angiographic adaptations. Comparative measurements of blood pressure (BP) were performed with a PORTAPRES® device sold by Finapres Medical System, and using Volume-Clamp method. The device was placed on subject's finger.

Figure 2:
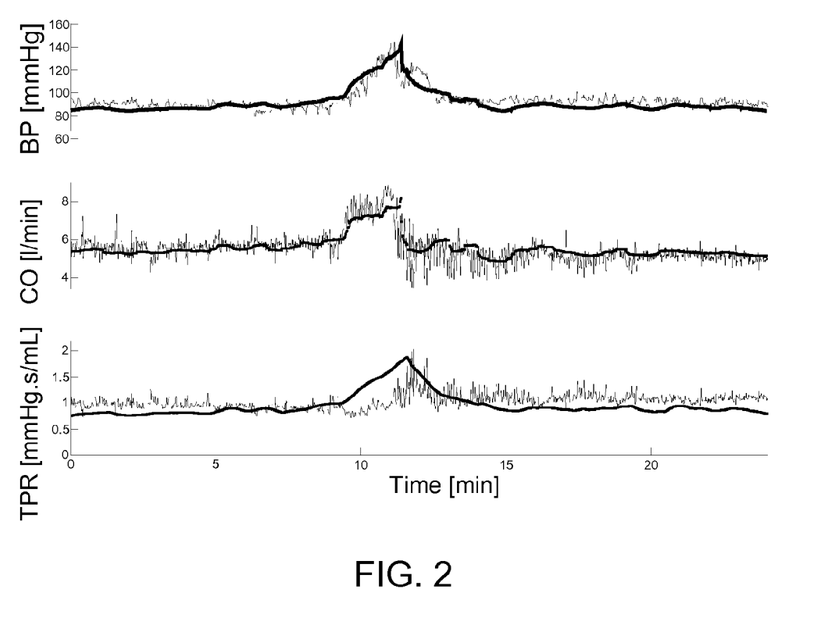
FIG. 2 is a diagram illustrating the values of blood pressure obtained with the method according to the present invention compared to a conventional Volume-Clamp method using finger blood pressure.

FIG. 2 represents, in bold, the three graphs given the blood pressure (BP), the Total Peripheral Resistance (TPR) and the Cardiac Output (CO) as a function of time, estimated by the method of the invention and in thin, those values obtained with the comparative PORTAPRES measurements.

The values estimated by the method of the invention perfectly tracked the values measured by the conventional method.

The method of the invention allows to obtain the desired parameters blood pressure (BP), Total Peripheral Resistance (TPR) and Cardiac Output (CO) only from the observations of some selected cardiovascular parameters HR, SV and PWV, and without using invasive technology.

What we claim is:

1. An apparatus for a continuous non-invasive and non-obtrusive monitoring of blood pressure, comprising:
   means for measuring a Pulse Wave parameter of a segment of an arterial tree of a subject, and for providing at least one signal representative of said Pulse Wave parameter;
   means for measuring a Cardiac Output parameter, and for providing at least one signal representative of said Cardiac Output parameter; and
   means for determining a value of blood pressure (BP) that satisfies $$BP = \underset{BP}{\mathrm{argmin}}\, d(PW, \widehat{PW}(CO, BP))$$

where PW is a measured value of the Pulse Wave parameter, $\widehat{PW}(CO,BP)$ corresponds to a predicted value of the Pulse Wave parameter computed according to a model of the segment of the arterial tree relating a value of the Cardiac Output parameter, a value of the Pulse Wave Velocity parameter and a value of the blood pressure, which enables to calculate said predicted value of the Pulse Wave parameter from a measured value (CO) of the Cardiac Output parameter and determined values (BP) of the blood pressure, and determination of the value of the blood pressure (BP) that minimizes a distance between the value of the measured Pulse Wave parameter and the predicted value of the Pulse Wave parameter is done without performing a blood pressure calibration measurement.

2. The apparatus according to claim 1, wherein a hypothesized value of the blood pressure is determined from a hypothesized value of at least one of geometric and elastic characteristics of the involved vessels in the segment of the arterial tree, and wherein said apparatus further comprises:
   means for hypothesizing a value of at least one of geometric and elastic characteristics of the involved vessels in the segment and, from said hypothesized value of said geometric and elastic characteristic, determining an expected value of the Pulse Wave parameter by using a model relating the Pulse Wave parameter, the Cardiac Output parameter and said geometric and elastic characteristic,
   means for comparing said expected Pulse Wave parameter value to said signal representative of the measured Pulse Wave parameter value and computing the distance between said expected Pulse Wave parameter value and said measured Pulse Wave parameter value (PW),
   means for repeating the determination of an expected value of the Pulse Wave parameter from a hypothesized value of said geometric and elastic characteristic and the comparison of said expected Pulse Wave parameter value to said signal representative of the measured Pulse Wave parameter value, until the distance between the Pulse Wave parameter value and the measured Pulse Wave parameter value is minimized in order to determine an estimated value of said geometric and elastic characteristic,
   means for determining the value (BP) of the blood pressure from said estimated value of said geometric and elastic characteristic by using a model relating the blood pressure, said Cardiac Output parameter, and said geometric and elastic characteristic,
   means for storing and/or displaying the determined value (BP) of the blood pressure.

3. The apparatus according to claim 1, wherein the Pulse Wave parameter is a Pulse Wave Velocity (PWV) parameter or a Pulse Transit Time (PTT) parameter.

4. The apparatus according to claim 2, wherein said geometric and elastic characteristic is the diameter of the vessels in the segment.

5. The apparatus according to claim 2, wherein the model relating the Pulse Wave parameter, the Cardiac Output parameter, and said geometric and elastic characteristic is theoretical.

6. The apparatus according to claim 2, wherein the model relating the blood pressure, the Cardiac Output parameter and said geometric and elastic characteristic is theoretical.

7. The apparatus according to claim 2, wherein the model relating the Pulse Wave parameter, the Cardiac Output parameter, and said geometric and elastic characteristic is empirical.

8. The apparatus according to claim 2, wherein the model relating the blood pressure, the Cardiac Output parameter, and said geometric and elastic characteristic is empirical.

9. The apparatus according to claim 1, wherein the means for measuring the Pulse Wave parameter use only optic and electric sensing technologies.

10. The apparatus according to claim 9, wherein the optic technology is Photoplethysmography (PPG) and the electric technologies are Electrocardiography (ECG) and Impedance Pleythysmography (IPG).

11. The apparatus according to claim 1, wherein means for measuring the Cardiac Output parameter use only electric sensing technologies.

12. The apparatus according to claim 11, wherein the electric technologies are Electrocardiography (ECG) and Impedance Pleythysmography (IPG).

13. The apparatus according to claim 1, wherein the apparatus further comprises means for computing a Total Peripheral Resistance (TPR) parameter from the determined value (BP) of the blood pressure.

14. The apparatus according to claim 13, wherein the means for storing and/or displaying the determined value (BP) of the blood pressure comprise means for simultaneously storing and/or displaying several cardiovascular parameters selected from the group comprising the determined Total Peripheral Resistance (TPR), the determined value (BP) of the blood pressure, the value (CO) of the Cardiac Output parameter.

15. An apparatus for a continuous non-invasive and non-obtrusive monitoring of blood pressure, comprising:

at least one of an optic sensor or an electric sensor configured for measuring a Pulse Wave parameter, and for providing at least one signal representative of said Pulse Wave parameter;

a sensor configured for measuring a Cardiac Output parameter, and for providing at least one signal representative of said Cardiac Output parameter; and a computing device configured for determining a value of blood pressure (BP) that satisfies $$BP = \underset{BP}{\operatorname{argmin}} d(PW, \widehat{PW}(CO, BP))$$

where PW is a measured value of the Pulse Wave parameter, $\widehat{PW}$ (CO,BP) corresponds to a predicted value of the Pulse Wave parameter computed according to a model of the segment of the arterial tree relating a value of the Cardiac Output parameter, a value of the Pulse Wave Velocity parameter and a value of the blood pressure, which enables to calculate said predicted value of the Pulse Wave parameter from a measured value (CO) of the Cardiac Output parameter and determined values (BP) of the blood pressure, and determination of the value of the blood pressure (BP) that minimizes a distance between the value of the measured Pulse Wave parameter and the predicted value of the Pulse Wave parameter is done without performing a blood pressure calibration measurement.

16. The apparatus according to claim 15, wherein the optic sensor comprises a Photoplethysmograph and the electric sensor comprises an Electrocardiograph or an Impedance Pleythysmograph.

17. The apparatus according to claim 15, wherein the sensor configured for measuring the Cardiac Output parameter comprises an Electrocardiograph or an Impedance Pleythysmograph.

\* \* \* \* \*